United States Patent [19]

Nysted

[11] 4,001,220

[45] Jan. 4, 1977

[54] 6-(AMINATED METHYL)-3β-OXY-5α-(CHOLESTANE-STIGMASTANE)-5,6-DIOLS, SALTS THEREOF, AND INTERMEDIATES THERETO

[75] Inventor: Leonard N. Nysted, Highland Park, Ill.

[73] Assignee: G. D. Searle & Co., Chicago, Ill.

[22] Filed: Jan. 27, 1976

[21] Appl. No.: 652,944

[52] U.S. Cl. .................... 260/239.55 R; 260/397.2
[51] Int. Cl.² ........................................ C07J 21/00
[58] Field of Search ............... 260/239.55 R, 397.2

[56] References Cited

UNITED STATES PATENTS

| | | | |
|---|---|---|---|
| 3,642,840 | 2/1972 | van Rheenan | 260/397.1 |
| 3,912,722 | 10/1975 | Mukawa | 260/397.2 |

*Primary Examiner*—Elbert L. Roberts
*Attorney, Agent, or Firm*—John M. Brown

[57] ABSTRACT

Preparation and the analgesic, antiulcerogenic, hypolipemic, and antimicrobial activity of 6-(aminated methyl)-3β-oxy-5α-(cholestane/stigmastane)-5,6-diols, salts thereof, and intermediates thereto are disclosed.

17 Claims, No Drawings

6-(AMINATED METHYL)-3β-OXY-5α-(CHOLESTANE-STIGMASTANE)-5,6-DIOLS, SALTS THEREOF, AND INTERMEDIATES THERETO

This invention relates to 6-(aminated methyl)-3β-oxy-5α-(cholestane/stigmastane)-5,6-diols, corresponding acid addition and quaternary ammonium salts, and the preparation thereof. More particularly, this invention provides new, useful, and unobvious steroidal bases of the formula

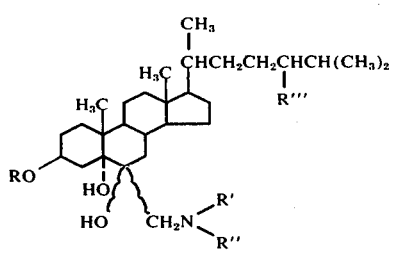

wherein R represents hydrogen or alkanoyl; R' and R'' each represent hydrogen, alkyl, or hydroxyalkyl; R''' represents hydrogen or ethyl; and the wavy lines signify that the 6-hydroxy and 6-aminated methyl substituents can be in the alpha and beta configurations, respectively, or vice versa.

The alkanoyl represented by R can be enformulated thus

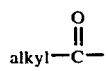

in which formula the alkyl constituent, like each alkyl represented by R' and R'', preferably contains fewer than 8 carbons. Illustrative of such alkyls are methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, and like monovalent, saturated, acyclic, straight- or branched-chain, hydrocarbon groupings of the formula

wherein, as indicated above, n advantageously represents a positive integer less than 8.

Each hydroxyalkyl represented by R' and R'' is preferably but not necessarily one wherein more than 1 and fewer than 6 carbons are present. Such hydroxyalkyls can be enformulated as —Alk—OH wherein Alk symbolizes alkylene typified by 1,2-ethanediyl, 1-methyl-1,2-ethanediyl, 1,1-dimethyl-1,2-ethanediyl, 1,1-propanediyl, 2-2-dimethyl-1,3-propanediyl, 1,4-butanediyl, or like bivalent, saturated, acyclic, straight- or branched-chain hydrocarbon grouping of the formula

in which m advantageously represents a positive integer greater than 1 and less than 6.

The compounds to which this invention relates are useful by reason of their valuable biological properties. For example, compounds having the structural formula hereinbefore set forth are analgesic, antiulcerogenic, hypolipemic, and antimicrobial, as also are (1) acid addition and quaternary ammonium salts thereof having the formula

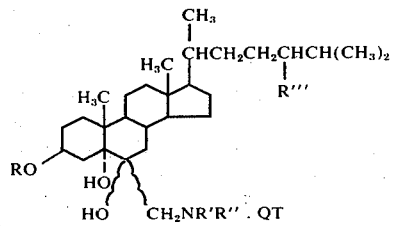

(2) intermediates of the formula

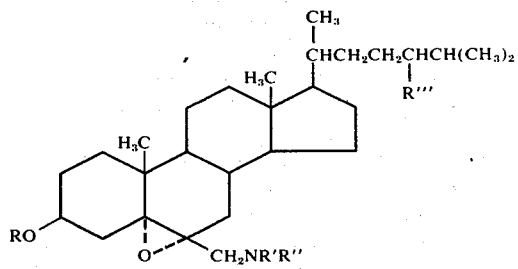

and (3) salts of the above-specified intermediates having the formula

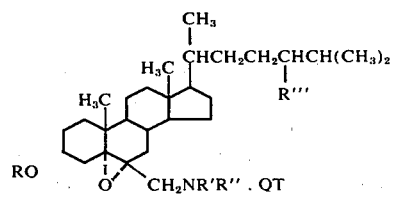

Wherever they appear in the three formulas immediately preceding, R, R', R'', R''', and the wavy lines retain the meanings previously assigned; Q represents hydrogen, alkyl optionally substituted by hydroxyl and preferably containing fewer than 8 carbons, alkenyl such as ethenyl and propenyl, or aralkyl such as benzyl and phenethyl; and T represents one equivalent of an anion — for example, chloride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, gluconate, ascorbate, benzoate, cinnamate, or the like — which, in combination with the cationic portion of a salt aforesaid, is neither biologically nor otherwise incompatible.

The analgesic utility of the instant compounds can be demonstrated via the standardized tests described in U.S. Pat. No. 3,692,799. So tested, 6α-(dimethylaminomethyl)-5α-cholestane-3β,5,6β-triol hydrochloride and 6β-(dimethylaminomethyl)-5,6α-epoxy-5α-cholestan-3β-ol, the products of Examples 2E and 4A hereinafter, were found active at 13 and 37 mg/kg, respectively.

The antiulcerogenic utility of the instant compounds can be demonstrated via the standardized test described in U.S. Pat. No. 3,483,192. So tested, 6β-(dimethylaminomethyl)-5,6α-epoxy-5α-cholestan-3β-ol and the product of Example 13C hereinafter, 6β-(aminomethyl)-5α-stigmastane-3β,5,6α-triol hydrochloride hemihydrate, were found active at 50 mg/kg.

The hypolipemic utility of the instant compounds can be demonstrated via the standardized test described in U.S. Pat. No. 3,843,660. So tested, 6α-(dimethylaminomethyl)-5α-cholestane-3β,5,6β-triol hydrochloride, 6β-(dimethylaminomethyl)-5,6α-epoxy-5α-cholestan-3β-ol, and 6β-(aminomethyl)-5α-stigmastane-3β,5,6α-triol hydrochloride hemihydrate were found active at 34, 48, and 42 mg/kg, respectively, The antimicrobial utility of the instant compounds can be demonstrated via the standardized test for their capacity to prevent the growth of *Erwinia sp.* and *Verticillium albo-atrum* described in U.S. Pat. No. 3,845,038. So tested, 6α-(dimethylaminomethyl)-5α-cholestane-3β-5,6β-triol hydrochloride, 6β-(dimethylaminomethyl)-5,6α-epoxy-5α-cholestan-3βol, and 6β-(aminomethyl)-5α-stigmastane-3β,5,6α-triol hydrochloride hemihydrate were found active at 1000, 100, and 10 mcgm/ml, respectively, versus E. sp., and at 1000, 10, and 1000 mcgm/ml, respectively, versus *V. albo-atrum*.

The antimicrobial utility of the instant compounds can be further demonstrated via the standardized test for their capacity to prevent the growth of *Ceratocystis ulmi* described in U.S. Pat. No 3,857,888, and a test identical therewith except for use of *C. fagacaerum* instead of *C. ulmi* as the involved microorganism. So tested, 6α-(dimethylaminomethyl)-5α-cholestane-3β-5,6β-triol hydrochloride was found active at 1000 mcgm/ml.

The activity of 6α-(dimethylaminomethyl)-5α-cholestane-3β,5,6β-triol hydrochloride, 6β-(dimethylamino-methyl)-5,6α-epoxy-5α-cholestan-3β-ol, and 6β-(aminomethyl)-5α-stigmastane-3β,5,6α-triol hydrochloride hemihydrate in various tests hereinbefore referred to is specified merely for purposes of illustration, and is accordingly not to be construed as either delimiting or exclusionary.

Preparation of the 6α-dialkylaminomethyl-6β-hydroxy bases of this invention can be effected by contacting a compound formula

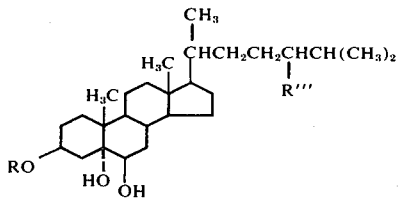

wherein R and R'''' are as previously defined, with chromium trioxide and sulfuric acid in acetone; contacting the resultant 6-one with the complex (U.S. Pat. No. 3,634,649, Ex. 2) formed in situ by heating activated zinc with dibromomethane in tetrahydrofuran under nitrogen, using aluminum isopropoxide to catalyze the complex formation; converting the resultant 6-methylene compound to the corresponding 6-halomethyl-5-ene by contacting it in cold dichloromethane with phosphorus tribromide or trichloride; contacting an ice-cold solution of the 6-halomethyl-5-ene in benzene with m-chloroperbenzoic acid during 30 minutes, then allowing the reactants to warm to room temperature during 3 hours; contacting the resultant 5α,6α-epoxy-6β-halomethyl compound with dialkylamine in benzene at room temperatures for 24 hours (using a sealed reaction vessel where volatility of the reaction mixture recommends it); and contacting the resultant 5α,6α-epoxy-6β-dialkylamino-methyl compound with perchloric acid in acetone at room temperatures for 1 hour, thereby cleaving the epoxy linkage and affording a compound of the formula

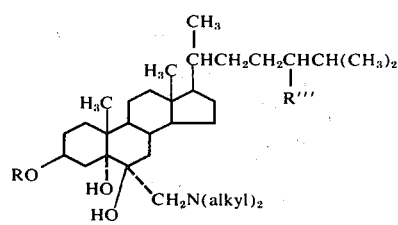

wherein R and R''' are defined as before except that R represents solely hydrogen if acetonic perchloric acid contact is extended to 48 hours. The triol which thereby eventuates can alternatively be prepared by cleaving the epoxy linkage in an appropriate 5α,6α-epoxy-6β-dialkylaminomethyl compound via perchloric acid in acetone subsequent to saponifying any ester linkage present via methanolic potassium bicarbonate at the boiling point. A further alternative route to such triol proceeds by 48-hour contact between the 5α,6α-epoxy-6β-halomethyl intermediate above referred to and perchloric acid in acetone, affording the corresponding 6β-halomethyl triol, which is contacted with dialkylamine in benzene at room temperatures during 24 hours (using a sealed reaction vessel if volatility recommends it) to produce the indicated product.

Preparation of the 6α-aminomethyl-6β-hydroxy bases of this invention proceeds via prolonged pressurized contact between a 6β-halomethyl triol aforesaid and liquid ammonia in benzene at room temperatures and, if desired, esterification of the 3β-hydroxyl in the resultant triol by contacting it with an alkanoic acid in dioxane containing hydrogen chloride.

Preparation of the 6α-di(hydroxyalkyl)aminomethyl-6β-hydroxy bases of this invention proceeds by heating a 5α,6α-epoxy-6β-halomethyl compound aforesaid — more particularly, such compound in which the halogen is bromine — with an iminodialkanol in dichloromethane for 24 hours and contacting the resultant epoxide with perchloric acid in acetone, affording the corresponding triol unless the starting material was 3-esterified and the duration of acetonic perchloric acid contact is relatively short, under which circumstances the ester linkage remains intact.

The 6α-hydroxy bases of this invention can be prepared by contacting an ice-cold dichloromethane solution of a 6-methylene compound (preparable as hereinbefore described) of the formula

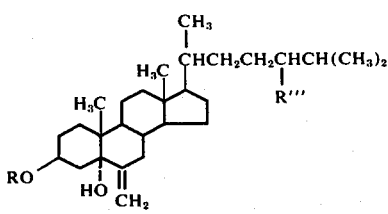

wherein R and R''' are as previously defined, with m-chloroperbenzoic acid during 30 minutes, then allowing the reactants to warm to room temperature during 3 hours; contacting the resultant spiro[oxirane-2,6'-steroid]

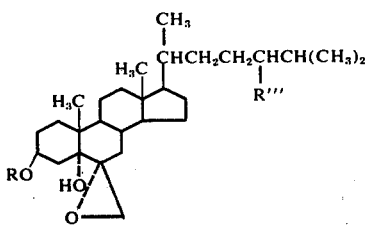

with liquid ammonia, a dialkylamine, or iminodialkarol, using a sealed reaction vessel if volatility of the reaction mixture recommends it, plus such solvent(s) and reaction temperature(s) as are adapted to afford the highest yields of product in the shortest periods of time; and, if desired, esterifying the 3β-hydroxyl in the resultant triol via the procedure outlined in the penultimate paragraph.

Each of the bases of this invention can be converted to a salt of the invention by contacting it — usually in the presence of an inert solvent such as chloroform, acetone, butanol, methanol, or the like — with one equivalent of an inorganic or strong organic acid, or an ester, having the formula

QT wherein the definition of Q and T remains as previously set forth. Quaternary salts are commonly prepared at temperatures ranging from 5°–100° C in from 1 hour to several days, using a sealed reaction vessel if volatility recommends it.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a mixture of 65 parts of powdered zinc and 145 parts of tetrahydrofuran at the boiling point under reflux in a nitrogen atmosphere is added, with stirring during 10 minutes, 35 parts of a 20% solution of hydrogen chloride in dioxane, followed after 20 minutes by 5 parts of aluminum isopropoxide. Approximately 5 minutes later, introduction of 70 parts of dibromomethane is commenced, the rate being such as to require approximately 2 ½ hours for completion. Heating at the boiling point under reflux with stirring is continued throughout this operation and for approximately 14 hours thereafter, at which point the temperature of the reaction mixture is lowered to −10° and 42 parts of 3β-acetoxy-5α-hydroxychol-estan-6-one [Shionogi Kenkusho Nempo, 10, 47 (1960)] is stirred in during 10 minutes. The reaction mixture is then warmed to room temperature during 1 hour and maintained thereat for a further 2 hours, stirring being continued throughout. At this point the temperature of the reaction mixture is again lowered, this time to around 5°, at which temperature 100 parts of aqueous 50% acetic acid is added — slowly for as long as gas evolution continues and rapidly thereafter. The temperature of the reaction mixture rises to around 28° during this operation. Insoluble solids are filtered out, and the filtrate is vigorously steam-distilled until the tacky solids which precipitate in the distilland become crystalline. The crystalline material is filtered from the hot distilland, washed with water, and sufficiently dried to be taken up in approximately 65 parts of dichloromethane. The dichloromethane solution is filtered through diatomaceous earth, which is then washed with 140 parts of acetone. Washings and filtrate are combined and distilled while 175 parts of water is slowly added. Crystallization occurs. Distillation is continued for a short time thereafter, whereupon the crystals are filtered off, washed well with aqueous 50% acetone, and dried in vacuo at 60°. The product thus isolated is 3β-(acetyloxy)-6-methylene-5α-cholestan-5-ol.

B. To a solution of 6 parts of phosphorus trichloride in 65 parts of dichloromethane at 0° is slowly added, with stirring, a solution of 12 parts of 3β-(acetyloxy)-6-methylene-5α-cholestan-5-ol in 65 parts of dichloromethane. When the addition is complete, stirring is continued while the temperature of the reaction mixture is increased to approximately 25° during 30 minutes. At this point, 105 parts of diethyl ether, followed — cautiously — by 100 parts of aqueous 10% sodium bicarbonate is mixed in. The organic phase is then separated, washed with aqueous 10% potassium bicarbonate, dried over anhydrous sodium sulfate and stripped of solvent by vacuum distillation. The residue is 6-(chloromethyl)cholest-5-en-3β-yl acetate, which can be further purified by trituration with 40 parts of methanol.

C. To a solution of 30 parts of 6-(chloromethyl)-cholest-5-en-3β-yl acetate in 175 parts of benzene at 0° is added 18 parts of 86% m-chloroperbenzoic acid. The resultant mixture is stirred at 0° for 30 minutes, then allowed to warm to room temperature with continued stirring during 3 hours. At this point, approximately 200 parts of hexane is introduced; and the solids which separate are filtered out. The filtrate is consecutively washed with aqueous 10% sodium bisulfate and aqueous 10% sodium bicarbonate, then dried over anhydrous sodium sulfate, and finally stripped of solvent by vacuum distillation at 25°. The residue is 6β-(chloromethyl)-5,6α-epoxy-5α-cholestan-3β-yl acetate.

D. To a solution of 10 parts of 6β-(chloromethyl)-5,6α-epoxy-5α-cholestan-3β-yl acetate in 120 parts of acetone at 35° is added, with stirring, 16 parts of 20% perchloric acid. Stirring is continued for 1 hour at 35°, whereupon the reactants are allowed to cool to room temperature during 48 hours. Sufficient water to initiate the precipitation of a crystalline solid is then introduced. The precipitate is 6α-(chloromethyl)-5α-cholestane-3β,5,6β-triol, which is isolated by filtration, washed with water, and dried in vacuo.

E. To a solution of 10 parts of 6α-(chloromethyl)-5α-cholestane-3β,5,6β-triol in 90 parts of benzene is added 14 parts of liquid ammonia. The resultant mixture is allowed to stand in a sealed vessel at room temperature for 21 days, whereupon the excess ammonia is vented and solvent stripped by vacuum distillation. The residue is washed by trituration with water, then crystallized from aqueous methanol. The product thus isolated is 6α-(aminomethyl)-5α-cholestane-3β,5,6β-triol, having the formula

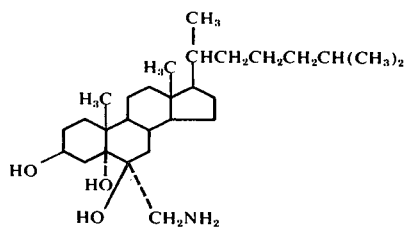

EXAMPLE 2

A. Substitution of 12 parts of phosphorus tribromide for the phosphorus trichloride called for in Example 1B affords, -(bromomethyl)-the procedure there detailed, 6-(bromomethyl)cholest-5-en-3β-yl acetate.

B. Substitution of 30 parts of 6-(bromomethyl)-cholest-5-en-3β-yl acetate for the 6-(chloromethyl)cholest-5-en-3β-yl acetate called for in Example 1C affords, by the procedure there detailed, 6β-(bromomethyl)-5,6α-epoxy-5α-cholestan-3β-yl acetate.

C. A mixture of 7 parts of dimethylamine and a solution of 10 parts of 6β-(bromoethyl)-5,6α-epoxy-5α-cholestan-3β-yl acetate in 90 parts of benzene is allowed to stand in a sealed vessel at room temperatures for 24 hours, whereupon the solid which precipitates is filtered out and the filtrate stripped of solvent by vacuum distillation. The residue is taken up in hexane. The hexane solution is filtered through diatomaceous earth, and the filtrate is stripped of solvent by vacuum distillation. The oil which remains is 6β-(dimethylaminomethyl)-5,6α-epoxy-5α-cholestan-3β-yl acetate. D. To a solution of 6 parts of 6β-(dimethylaminomethyl)-5,6α-epoxy-5α-cholestan-3β-yl acetate in 120 parts of acetone is added approximately 17 parts of perchloric acid. The resultant solution is warmed to 35°, then stirred while cooling to room temperature during 1 hour. The resultant mixture is allowed to stand for 48 hours, whereupon 10 parts of potassium bicarbonate followed cautiously by 200 parts of water is introduced. The solid which precipitates is filtered off, washed with water, and dried in air. The product thus isolated is 6α-(dimethylaminomethyl)-5α-cholestane-3β,5,6β-triol.

E. A solution of 10 parts of 6α-(dimethylaminomethyl)-5α-cholestane-3β,5,6β-triol in 20 parts of 2-propanol is acidified with a 20% solution of hydrogen chloride in dioxane. The resultant solution is diluted to the point of incipient precipitation with ethyl acetate. The crystalline solid which forms on standing is isolated by filtration, washed with ethyl acetate, and dried in vacuo at 65°. The product thus obtained is 6α-(dimethylaminomethyl)-5α-cholestane-3β,5, 6β-triol hydrochloride..

F. Approximately 5 parts of methyl bromide is introduced beneath the surface of a solution of 10 parts of 6α-(dimethylaminomethyl)-5α-cholestane-3β,5,6β-triol in approximately 15 parts of acetone. The resultant mixture is allowed to stand in a sealed vessel for 24 hours, at which point the solid which has separated is isolated by filtration, washed with ethyl acetate, and dried in vacuo at 50°. The product thus obtained is 6α-(trimethylammoniomethyl)-5α-cholestane-3β,5,6β-triol bromide, having the formula

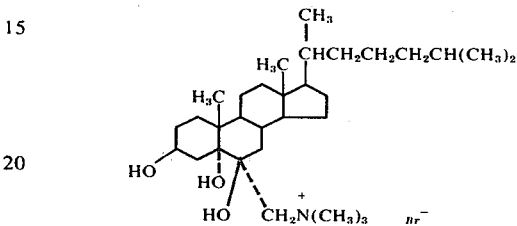

G. Substitution of approximately 12 parts of methyl iodide for the methyl bromide called for in the preceding Part F of this example affords, by the procedure there detailed, 6α-(trimethylammoniomethyl)-5α-cholestane-3β,5,6β-triol iodide.

EXAMPLE 3

To a solution of 4 parts of 6β-(dimethylaminomethyl)-5,6αepoxy-5α-cholestan-3β-yl acetate in 80 parts of acetone at room temperature is added 11 parts of 20% perchloric acid. The resultant mixture is stirred at room temperatures for 1 hour, whereupon 100 parts of water followed cautiously by 5 parts of potassium bicarbonate is introduced. Sufficient additional water to triple the volume of the initial reaction mixture is then added; and the solid which thereafter precipitates is isolated by filtration, washed with water, and dried in air. The product thus obtained is 3β-(acetyloxy)-6α-(dimethylaminomethyl)-5α-cholestane-5,6β-diol.

EXAMPLE 4

A. To a solution of 7 parts of 6β-(dimethylaminomethyl)-5,6α-epoxy-5α-cholestan-3β-yl acetate in 32 parts of methanol at room temperature is added 10 parts of aqueous 40% potassium carbonate. The resultant mixture is allowed to stand for 24 hours, at which point 200 parts of water is mixed in. The solid precipitate thrown down is filtered off and taken up in dichloromethane. The dichloromethane solution is washed with water, dried over anhydrous sodium sulfate, and stripped of solvent by vacuum distillation. The residue is further purified by trituration with methanol, then dried in air. The product thus isolated is 6β-(dimethylaminomethyl)-5,6α-epoxy-5α-cholestan-3β-ol.

B. To a solution of 6 parts of 6β-(dimethylaminomethyl)-5,6α-epoxy-5α-cholestan-3β-ol in 120 parts of acetone is added approximately 17 parts of 20% perchloric acid. The resultant solution is warmed to 35°, then stirred for 1 hour while cooling to room temperature. Addition of 5 parts of potassium bicarbonate followed by cautious introduction of 200 parts of water causes precipitation of a solid, which is isolated by filtration and dried in air. The product thus obtained is 6α-(dimethylaminomethyl)-5α-cholestane-3β,5,6β- triol, identical with that produced by the procedure of Example 2D.

EXAMPLE 5

A. To a solution of 10 parts of 6β-(bromomethyl)-5,6α-epoxy-5α-cholestan-3β-yl acetate in approximately 45 parts of benzene is added 7 parts of diethylamine. The resultant mixture is allowed to stand at 30° for 72 hours, whereupon solvent and excess amine are removed by vacuum distillation. The residue is extracted with hexane. The hexane extract is filtered through diatomaceous earth. Removal of solvent from the filtrate by vacuum distillation leaves 6β-(diethylaminomethyl)-5,6α-epoxy-5α-cholestan-3β-yl acetate, an oil.

B. To a solution of 10 parts of 6β-(diethylaminomethyl)-5,6α-epoxy-5α-cholestan-3β-yl acetate in 80 parts of methanol is added 5 parts of potassium bicarbonate. The resultant mixture is heated at the boiling point under reflux for 1 ½ hours, whereupon sufficient water is introduced to cause precipitation of an amorphous solid. The precipitated reaction mixture is extracted with ethyl acetate. The ethyl acetate extract is washed with water, dried over anhydrous sodium sulfate, and stripped of solvent by vacuum distillation. The residual oil is 6β-(diethylaminomethyl)-5,6α-epoxy-5α-cholestan-3β-ol.

C. Substitution of 4 parts of 6β-(diethylaminomethyl)-5,6α-epoxy-5α-cholestan-3β-ol for the 6β-(dimethylamino-methyl)-5,6α-epoxy-5αchlorestan-3β-yl acetate called for in Example 3 affords, by the procedure there detailed, 6α-(diethylaminomethyl)-5α-cholestane-3β,5,6β-triol.

EXAMPLE 6

A. A solution of 10 parts of 6β-(bromomethyl)-5,6α-epoxy-5α-cholestan-3β-yl acetate in 10 parts of 2,2'-iminodiethanol and 27 parts of dichloromethane is heated at approximately 50° for 24 hours, whereupon the dichloromethane is removed by vacuum distillation and a solution of 4 parts of sodium hydroxide in 20 parts of water followed by 40 parts of 2-propanol is added to the residue. The resultant mixture is stirred at room temperatures for 3 hours, at which point the 2-propanol is removed by vacuum distillation. The residue is partitioned between water and chloroform. The chloroform phase is separated, washed with water, and stripped of solvent by vacuum distillation. The oily residue is 5,6α-epoxy-6β-[bis(2-hydroxyethyl)aminomethyl]-5α-cholestan-3β-ol.

B. Substitution of 10 parts of 5,6α-epoxy-6β-[bis(2-hydroxyethyl)aminomethyl]-5α-cholestan-3β-ol for the 6α-(dimethylaminomethyl)-5α-cholestane-3β,5,6β-triol called for in Example 2F affords, by the procedure there detailed, 5,6α-epoxy-6β-[bis(2-hydroxyethyl)methylammoniomethyl]-5α-cholestan-3β-ol bromide.

C. Substitution of 6 parts of 5,6α-epoxy-6β-[bis(2-hydroxyethyl)aminomethyl]-5α-cholestan-3β-ol for the 6β-(dimethylaminomethyl)-5,6α-epoxy-5α-cholestan-3βol called for in Example 4B affords, by the procedure there detailed, 6α-[bis(2-hydroxyethyl)aminomethyl]-5α-cholestane-3β,5,6β-triol. The product has the formula

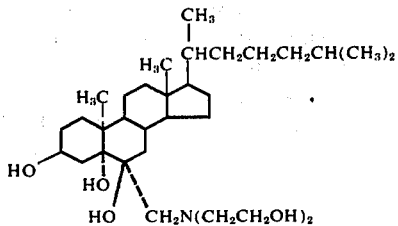

EXAMPLE 7

A. Substitution of 10 parts of 5,5'-iminobis-pentanol [Compt.rend., 252, 1624 (1961)]for the 2,2'-iminodicthanol called for in Example 6A affords, by the procedure there detailed, 5,6α-[bis-(5-hydroxypentyl-)aminomethyl]-5α-cholestan-3β-ol.

B. Substitution of 6 parts of 5,6α-epoxy-6β-[bis(5-hydroxypentyl)aminomethyl]-5α-cholestan-3β-ol for the 6β-(dimethylaminomethyl)-5,6α-epoxy-5α-cholestan-3β-ol called for in Example 4B affords, by the procedure there detailed, 6α-[bis(5-hydroxypentyl)aminomethyl]-5α-cholestane-3β,5,6β-triol.

EXAMPLE 8

A. To a suspension of 40 parts of 3β-(acetyloxy)-5α-stigmastane-5,6β-diol (U.S. Pat. No. 3,356,676) in 640 parts of acetone at 0°–5° is added, with continuous stirring during approximately 5 minutes, 102 parts of a mixture prepared by dissolving 10 parts of chromium trioxide in 20 parts of water and consecutively adding thereto 15 parts of concentrated sulfuric acid and 20 parts of water. Stirring at 0°–5° is continued for 25 minutes after the addition is complete, at which point 20 parts of 2-propanol is introduced and stirring then resumed for 15 minutes. Solids which separate are removed by filtration, and the filtrate is diluted with approximately 200 parts of water. Acetone is removed by vacuum distillation; and the solids which thereupon precipitate are filtered off, washed with water, and dried in air. The product thus isolated is 3β-(acetyloxy)-5-hydroxy-5α-stigmastan-6-one.

B. To a mixture of 65 parts of powdered zinc and 145 parts of tetrahydrofuran at the boiling point under reflux in a nitrogen atmosphere is added, with stirring during 10 minutes, 35 parts of a 20% solution of hydrogen chloride in dioxane, followed after 20 minutes by 5 parts of aluminum isopropoxide. Approximately 5 minutes later, introduction of 70 parts of dibromomethane is commenced, the rate being such as to require approximately 2 ½ hours for completion. Heating at the boiling point under reflux with stirring is continued throughout this operation and for approximately 14 hours thereafter, at which point the temperature of the reaction mixture is lowered to −10° and 42 parts of 3β-(acetyloxy)-5-hydroxy-5α-stigmastan-6-one is stirred in during 10 minutes. The reaction mixture is then warmed to room temperature during 1 hour and maintained thereat for a further 2 hours, stirring being continued throughout. At this point, the temperature of the reaction mixture is again lowered, this time to around 5°, at which temperature 100 parts of aqueous 50% acetic acid added — slowly for as long as gas evolution continues and rapidly thereafter. The temperature of the reaction mixture rises to around 28° during this operation. Insoluble solids are filtered out, and the filtrate is vigorously steam-distilled until the tacky solids which precipitate in the distilland become crystalline. The crystalline material is filtered from the hot distilland, washed with water, and sufficiently dried to be taken up in approximately 65 parts of dichloromethane. The dichloromethane solution is filtered through diatomaceous earth, which is then washed with 140 parts of acetone. Washings and filtrate are combined and distilled while 175 parts of water is slowly added. Crystallization occurs. Distillation is continued for a short time thereafter, whereupon the crystals are filtered off, washed well with aqueous 50% acetone, and dried in vacuo at 60°. The product thus isolated is 3β-(acetyloxy)-6-methylene-5α-stigmastan-5-ol.

C. Substitution of 12 parts of 3β-(acetyloxy)-6-methylene-5α-stigmastan-5-ol and 12 parts of phosphorous tribromide for the 3β-acetyloxy-6-methylene-5α-cholestan-5-ol and phosphorous trichloride, respectively, called for in Example 1B affords, by the procedure there detailed, 6-(bromomethyl)stigmast-5-en-3β-yl acetate.

D. Substitution of 30 parts of 6-(bromomethyl)-stigmast-5-en-3β-yl acetate for the 6-(chloromethyl)cholest-5-en-3β-yl acetate called for in Example 1C affords, by the procedure there detailed, 6β-(bromomethyl)-5,6β-epoxy-5α-stigmastan-3β-yl acetate.

E. Substitution of 10 parts of 6β-(bromomethyl)-5,6α-epoxy-5α-stigmastan-3β-yl acetate for the 6β-(bromomethyl)-5,6α-epoxy-5α-cholestan-3β-yl acetate called for in Example 5A affords, by the procedure there detailed, 6β-(dimethylaminomethyl)-5,6α-epoxy-5α-stigmastan-3β-yl acetate.

F. Substitution of 6 parts of 6β-(dimethylaminomethyl)-5,6α-epoxy-5α-stigmastan-3β-yl acetate for the 6β-(dimethylaminomethyl)-5,6α-epoxy-5α-cholestan-3β-yl acetate called for in Example 2D affords, by the procedure there detailed 6α-(dimethylaminomethyl)-5α-stigmastane-3β,5,6β-triol. The product has the formula

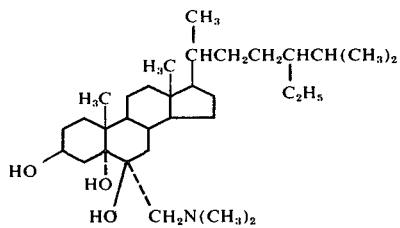

EXAMPLE 9

A. Substitution of 30 parts of 3β-(acetyloxy)-6-methylene-5α-cholestan-5-ol for the 6-(chloromethyl)-cholest-5-en-3β-yl acetate called for in Example 1C affords, by the procedure there detailed, (5α,6α)-3β-(acetyloxy)-spiro[cholestan-6,2'-oxiran]-5-ol, having the formula

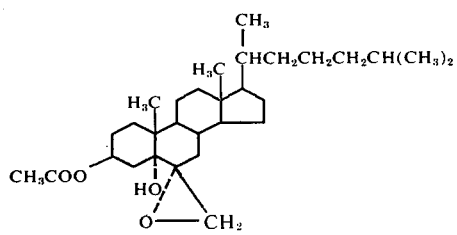

B. To a solution of 12 parts of (5α,6α)-3β-(acetyloxy)spiro[cholestan-6,2'-oxiran]-5-ol in 45 parts of benzene is added 20 parts of methanol and 7 parts of liquid ammonia. The resultant mixture is maintained in a sealed vessel at 150° for 6 days, whereupon it is cooled and vented, after which solvents are removed by vacuum distillation. The residue is 6β-(aminomethyl)-5α-cholestane-3β,5,6α-triol. The product has the formula

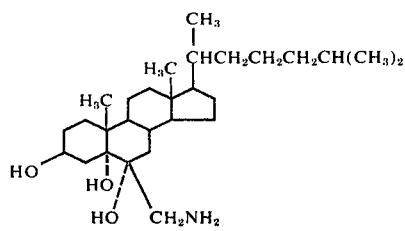

C. A solution of 12 parts of 6β-(aminomethyl)-5α-cholestane-3β,5,6α-triol in 40 parts of 2-propanol is acidified with 25 parts of a 20% solution of hydrogen chloride in dioxane, whereupon a quantity of ether sufficient to bring the solution to the point of incipient precipitation is introduced. The precipitate which thereupon forms is filtered off, washed with ether, and further purified by recrystallization from a mixture of methanol and ether. The product thus isolated is 6β-(aminomethyl)-5α-cholestane-3β,5,6α-triol hydrochloride.

EXAMPLE 10

A. To a solution of 12 parts of (5α,6α)-3β-(acetyloxy)spiro[cholestan-6,2'-oxiran]-5-ol in 45 parts of benzene is added 20 parts of methanol and 7 parts of dimethylamine. The resultant mixture is maintained in a sealed vessel at 150° for 96 hours, whereupon it is cooled and vented. Solvents are then removed by vacuum distillation. The residue is 6β-(dimethylaminomethyl)-5α-cholestane-3β,5,6α-triol.

B. Substitution of 12 parts of 6β-(dimethylaminomethyl)-5α-cholestane-3β,5,6α-triol for the 6β-(aminomethyl)-5α-cholestane-3β,5,6α-triol called for in Example 9C affords, by the procedure there detailed, 6β-(dimethylaminomethyl)-5α-cholestane-3β,5,6α-triol hydrochloride. The product can be reconverted to the free base by dissolving approximately 10 parts thereof in 80 parts of methanol and consecutively adding to the solution 7 parts of liquid dimethylamine and 200 parts of water. The solids thrown down are filtered off, washed with water, and dried in vacuo at 60°. The material thus obtained is 6β-(dimethylaminomethyl)-5α-cholestane-3β,5,6α-triol.

C. Substitution of 10 parts of 6β-(dimethylaminomethyl)-5α-cholestane-3β,5,6α-triol for the 6α-(dimethylaminomethyl)-5α-cholestane-3α,5,6β-triol called for in Example 2F affords, by the procedure there detailed, 6β-(trimethylammoniomethyl)-5α-cholestane-3β,5,6β-triol bromide.

EXAMPLE 11

To a solution of 5 parts of 6β-(dimethylaminomethyl)-5α-cholestane-3β,5,6α-triol in 20 parts of pyridine is added 10 parts of propionic anhydride. The resultant mixture is allowed to stand at room temperature for 24 hours, whereupon 5 parts of potassium bicarbonate cautiously followed by 100 parts of water is introduced. The oil that separates is extracted with ethyl acetate. The ethyl acetate extract is washed with water, dried over anhydrous sodium sulfate, and stripped of solvent by vacuum distillation. The residue is 6β-(dimethylaminomethyl)-3β-(propionyloxy)-5α-cholestane-5,6α-diol.

EXAMPLE 12

Substitution of 7 parts of diethylamine for the dimethylamine called for in Example 10A affords, by the procedure there detailed, 6β-(diethylaminomethyl)-5α-cholestane-3β,5,6α-triol.

EXAMPLE 13

A. Substitution of 30 parts of 3β-(acetyloxy)-6-methylene-5α-stigmastan-5-ol for the 6-(chloromethyl)-cholest-5-en-3β-yl acetate called for in Example 1C affords, by the procedure there detailed, (5'α,6'α)-3'β-(acetyloxy)spiro[oxirane-2,6'-stigmastan]-5'-ol.

B. Substitution of 12 parts of (5'α,6'α)-3'β-(acetyloxy)spiro[oxirane-2,6'-stigmastan]-5'-ol for the (5α,6α)-3β-(acetyloxy)spiro[cholestan-6,2'-oxiran]-5-ol called for in Example 9B affords, by the procedure there detailed, 6β-(aminomethyl)-5α-stigmastane-3β,5,6α-triol.

C. Substitution of 12 parts of 6β-(aminomethyl)-5α-stigmastane-3β,5,6α-triol for the 6β-(aminomethyl)-5α-cholestane-3β,5,6α-triol called for in Example 9C affords, by the procedure detailed, 6β-(aminomethyl)-5α-stigmastane-3β,5,6α-triol hydrochloride hemihydrate. The water of crystallization results from the hygroscopicity of the anhydrous salt, and can be removed by warming the hemihydrate in vacuo.

EXAMPLE 14

Substitution of 12 parts of (5'α,6'α)-3'β-(acetyloxy)spiro[oxirane-2,6'-stigmastan]-5'-ol for the (5α,6α)-3β-(acetyloxy)spiro[cholestan-6,2'-oxiran]-5-ol called for in Example 10A affords, by the procedure there detailed, 6β-(dimethylaminomethyl)-5α-stigmastane-3β,5,6α-triol.

What is claimed is:

1. A compound of the formula

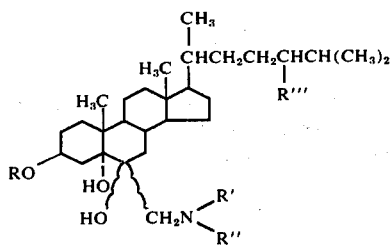

wherein R represents hydrogen or alkanoyl containing fewer than 9 carbons; R' and R" each represent hydrogen, alkyl containing fewer than 8 carbons, or hydroxyalkyl of the formula —Alk—OH in which Alk represents alkylene containing more than 1 and fewer than 6 carbons; R''' represents hydrogen or ethyl; and the wavy lines indicate that the 6-hydroxy and 6-aminated methyl substituents can be in the alpha and beta configurations, respectively, or vice versa.

2. A compound according to claim 1 which is 6α-(aminomethyl)-5α-cholestane-3β,5,6β-triol.

3. A compound according to claim 1 having the formula

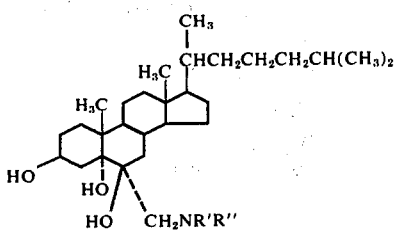

wherein R' and R" each represent alkyl containing fewer than 8 carbons.

4. A compound according to claim 1 which is 6α-(dimethylaminomethyl)-5α-cholestane-3β,5,6β-triol.

5. A compound according to claim 1 having the formula

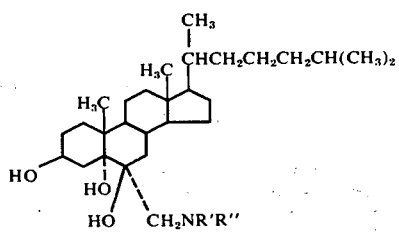

wherein R' and R" each represent hydroxyalkyl of the formula

—Alk—OH in which Alk represents alkylene containing more than 1 and fewer than 6 carbons.

6. A compound according to claim 1 which is 6α-[bis(2-hydroxyethyl)aminomethyl]-5α-cholestane-3β,5,6β-triol.

7. A compound according to claim 1 having the formula

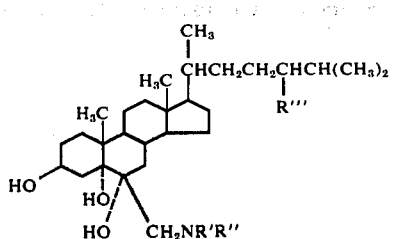

wherein R' and R" each represent hydrogen or alkyl containing fewer than 8 carbons and R''' represents hydrogen or ethyl.

8. A compound according to claim 1 which is 6β-(aminomethyl)-5α-cholestane-3β,5,6α-triol.

9. A compound according to claim 1 having the formula

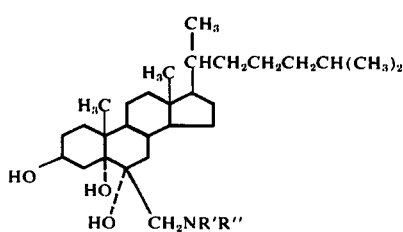

wherein R' and R" each represent alkyl containing fewer than 8 carbons.

10. A compound according to claim 1 which is 6β-(dimethylaminomethyl)-5α-cholestane-3β,5,6α-triol.

11. A compound according to claim 1 which is 6β-(aminomethyl)-5α-stigmastane-3β,5,6α-triol.

12. A compound of the formula

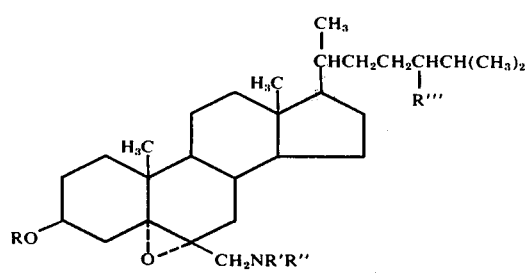

wherein R represents hydrogen or acetyl; R' and R" each represent hydrogen, alkyl containing fewer than 8 carbons, or hydroxyalkyl of the formula —Alk—OH in which Alk represent alkylene containing more than 1 and fewer than 6 carbons; and R''' represents hydrogen or ethyl.

13. A compound according to claim 12 having the formula

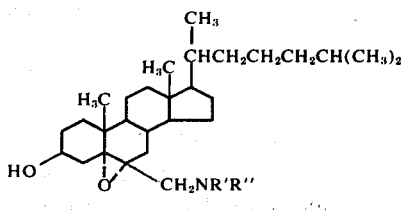

wherein R' and R" each represent alkyl containing fewer than 8 carbons.

14. A compound according to claim 12 which is 6β-(dimethylaminomethyl)-5,6α-epoxy-5α-cholestan-3β-ol.

15. A compound according to claim 12 having the formula

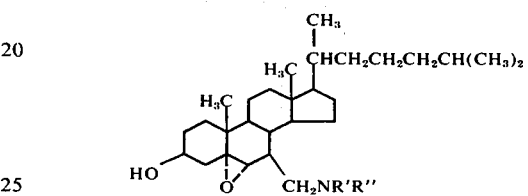

wherein R' and R" each represent hydroxyalkyl of the formula

—Alk—OH in which Alk represents alkylene containing more than 1 and fewer than 6 carbons.

16. A compound according to claim 12 which is 5,6α-epoxy-6β-[bis(2-hydroxyethyl)aminomethyl]-5α-cholestan-3β-ol.

17. A compound of the formula

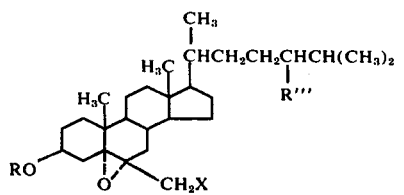

wherein R represents alkanoyl containing fewer than 9 carbons, R''' represents hydrogen or ethyl, and X represents chlorine or bromine.

* * * * *

UNITED STATES PATENT AND TRADEMARK OFFICE
CERTIFICATE OF CORRECTION

PATENT NO. : 4,001,220
DATED : Jan. 4, 1977
INVENTOR(S) : Leonard N. Nysted

It is certified that error appears in the above-identified patent and that said Letters Patent are hereby corrected as shown below:

Column 3, line 57, "R''''" should read -- R''' --.

Column 5, lines 28 and 29, "iminodialkarol" should read -- iminodialkanol --.

Column 7, line 30, "affords, -(bromomethyl)-the" should read -- affords, by the --.

Column 9, line 32, "5αchlorestan" should read -- 5α-cholestan --.

Signed and Sealed this

Twenty-fourth Day of May 1977

[SEAL]

Attest:

RUTH C. MASON
*Attesting Officer*

C. MARSHALL DANN
*Commissioner of Patents and Trademarks*